US010969571B2

(12) United States Patent
Swanson

(10) Patent No.: US 10,969,571 B2
(45) Date of Patent: Apr. 6, 2021

(54) FEW-MODE FIBER ENDOSCOPE

(71) Applicant: Eric Swanson, Gloucester, MA (US)

(72) Inventor: Eric Swanson, Gloucester, MA (US)

(73) Assignee: Eric Swanson, Gloucester, MA (US)

(*) Notice: Subject to any disclaimer, the term of this patent is extended or adjusted under 35 U.S.C. 154(b) by 0 days.

(21) Appl. No.: 15/168,189

(22) Filed: May 30, 2016

(65) Prior Publication Data

US 2017/0343791 A1    Nov. 30, 2017

(51) Int. Cl.
  *G02B 23/24* (2006.01)
  *G02B 23/26* (2006.01)
  (Continued)

(52) U.S. Cl.
  CPC ...... *G02B 23/2469* (2013.01); *A61B 1/00163* (2013.01); *A61B 1/00165* (2013.01); *A61B 5/0066* (2013.01); *A61B 5/0084* (2013.01); *G01B 9/02004* (2013.01); *G01B 9/02091* (2013.01); *G02B 6/0288* (2013.01); *G02B 23/26* (2013.01); *A61B 1/00172* (2013.01); *A61B 1/07* (2013.01); *A61B 5/0071* (2013.01); *A61B 5/0075* (2013.01); *G01N 21/4795* (2013.01); *G01N 21/65* (2013.01); *G01N 2021/6484* (2013.01); *G02B 6/2861* (2013.01)

(58) Field of Classification Search
  CPC . A61B 1/00009; A61B 1/00096; A61B 1/063; A61B 1/07; A61B 5/0066; A61B 5/0071; A61B 5/0084; G01B 9/02004; G01B 9/0209; G01N 21/954; G01N 2021/9546; G02B 6/14; G02B 6/2861; G02B 6/34; G02B 23/2423; G02B 23/2446; G02B 23/2469; G02B 23/26

See application file for complete search history.

(56) References Cited

U.S. PATENT DOCUMENTS 5,062,150 A * 10/1991 Swanson ............... H04B 10/118
                                                  250/203.1
5,321,501 A *  6/1994 Swanson ............ A61B 1/00096
                                                  250/227.27

(Continued)

FOREIGN PATENT DOCUMENTS

AU    1977597 A  *  9/1997  ......... A61B 1/00096
EP    0883793 A1 * 12/1998  ......... A61B 1/00096

(Continued)

OTHER PUBLICATIONS

Finalists for the European Inventor Award 2017, available at https://www.epo.org/learning-events/european-inventor/finalists/2017/fujimoto.html.*

(Continued)

*Primary Examiner* — Peter Radkowski
(74) *Attorney, Agent, or Firm* — Kurt Rauschenbach; Rauschenbach Patent Law Group, PLLC

(57) ABSTRACT

Disclosed herein are configurations for few-mode fiber optical endoscope systems employing distal optics and few-mode, double-clad or other optical fiber wherein the systems directing an optical beam to a sample via the optical fiber; collecting light backscattered from the sample; direct the backscattered light to a detector via the optical fiber; and detect the backscattered light; wherein the directed optical beam is single mode and the collected light is one or more higher order modes.

13 Claims, 9 Drawing Sheets

(51) Int. Cl.
*G01B 9/02* (2006.01)
*A61B 5/00* (2006.01)
*G02B 6/028* (2006.01)
*A61B 1/00* (2006.01)
G02B 6/28 (2006.01)
A61B 1/07 (2006.01)
G01N 21/47 (2006.01)
G01N 21/65 (2006.01)
G01N 21/64 (2006.01)

(56) References Cited

U.S. PATENT DOCUMENTS

| | | | | |
|---|---|---|---|---|
| 5,459,570 A * | 10/1995 | Swanson | A61B 1/00096 356/479 |
| 5,465,147 A * | 11/1995 | Swanson | A61B 1/00183 356/497 |
| 5,619,368 A * | 4/1997 | Swanson | G02F 1/3536 359/326 |
| 5,748,598 A * | 5/1998 | Swanson | A61B 1/00183 369/100 |
| 5,784,352 A * | 7/1998 | Swanson | A61B 5/0066 369/100 |
| 5,956,355 A * | 9/1999 | Swanson | A61B 1/00183 356/479 |
| 6,134,003 A * | 10/2000 | Tearney | A61B 1/00096 356/479 |
| 6,160,826 A * | 12/2000 | Swanson | A61B 1/00183 372/102 |
| 6,191,862 B1 * | 2/2001 | Swanson | G01B 11/2441 356/479 |
| 6,288,784 B1 * | 9/2001 | Hitzenberger | A61B 3/102 356/485 |
| 6,445,939 B1 * | 9/2002 | Swanson | A61B 5/0066 385/33 |
| 6,485,413 B1 * | 11/2002 | Boppart | A61B 1/00096 356/450 |
| 6,501,551 B1 * | 12/2002 | Tearney | A61B 1/00096 356/477 |
| 6,552,797 B2 * | 4/2003 | Swanson | G01N 21/4795 356/479 |
| 6,564,087 B1 * | 5/2003 | Pitris | A61B 1/00183 600/478 |
| 6,665,068 B1 * | 12/2003 | Schoeppe | G02B 27/283 356/300 |
| 6,891,984 B2 * | 5/2005 | Petersen | A61B 5/0066 385/117 |
| 7,061,618 B2 * | 6/2006 | Atia | G01J 3/10 356/454 |
| 7,366,365 B2 * | 4/2008 | Carver | A61B 5/0068 356/326 |
| 7,418,169 B2 * | 8/2008 | Tearney | A61B 1/00082 385/11 |
| 7,447,408 B2 * | 11/2008 | Bouma | G02B 6/02042 356/300 |
| 7,530,948 B2 * | 5/2009 | Seibel | A61B 1/0008 600/129 |
| 7,538,859 B2 * | 5/2009 | Tearney | A61B 5/0066 356/35.5 |
| 7,809,225 B2 * | 10/2010 | Bouma | G02B 6/02042 385/116 |
| 7,809,226 B2 * | 10/2010 | Bouma | G02B 6/02042 385/116 |
| 7,843,572 B2 * | 11/2010 | Tearney | A61B 5/0062 356/479 |
| 7,847,949 B2 * | 12/2010 | Tearney | A61B 5/0062 356/477 |
| 7,864,822 B2 * | 1/2011 | Bouma | A61B 5/0059 372/20 |
| 7,889,348 B2 * | 2/2011 | Tearney | A61B 1/043 356/311 |
| 7,916,387 B2 * | 3/2011 | Schmitt | A61B 5/0066 359/344 |
| 7,925,133 B2 * | 4/2011 | Bouma | G02B 6/02042 385/123 |
| 8,078,245 B2 * | 12/2011 | Daly | A61B 3/1005 356/124 |
| 8,149,418 B2 * | 4/2012 | Tearney | A61B 5/0062 356/479 |
| 8,300,230 B2 * | 10/2012 | Galle | G01M 11/3163 356/477 |
| 8,369,669 B2 * | 2/2013 | Bouma | G02B 6/02042 385/116 |
| 8,384,907 B2 * | 2/2013 | Tearney | A61B 5/0062 356/456 |
| 8,384,909 B2 * | 2/2013 | Yun | A61B 5/0059 356/479 |
| 8,416,818 B2 * | 4/2013 | Bouma | A61B 5/0059 372/20 |
| 8,437,007 B2 * | 5/2013 | Flanders | G01B 9/02004 356/479 |
| 8,515,221 B2 | 8/2013 | Flanders | |
| 8,676,013 B2 * | 3/2014 | Bouma | G02B 6/02042 385/115 |
| 8,690,330 B2 | 4/2014 | Hacker et al. | |
| 8,711,364 B2 * | 4/2014 | Brennan | A61B 3/102 356/479 |
| 8,760,663 B2 * | 6/2014 | Tearney | A61B 5/0062 356/479 |
| 8,822,905 B2 * | 9/2014 | Ryf | G02B 6/4206 250/216 |
| 8,838,213 B2 * | 9/2014 | Tearney | A61B 18/22 356/305 |
| 8,854,629 B2 * | 10/2014 | Frisken | G01N 21/4795 356/491 |
| 8,947,648 B2 * | 2/2015 | Swanson | G01B 9/02004 356/28 |
| 8,994,954 B2 * | 3/2015 | Atia | G01B 9/02004 356/479 |
| 9,008,142 B2 * | 4/2015 | Minneman | H01S 5/0652 372/20 |
| 9,044,164 B2 | 6/2015 | Hacker et al. | |
| 9,140,854 B2 * | 9/2015 | Doerr | G02B 6/12009 |
| 9,162,404 B2 * | 10/2015 | Doerr | B29D 11/00663 |
| 9,186,066 B2 * | 11/2015 | Tearney | A61B 5/0066 |
| 9,186,067 B2 * | 11/2015 | Tearney | A61B 5/0066 |
| 9,254,089 B2 * | 2/2016 | Tearney | A61B 5/0062 |
| 9,304,121 B2 * | 4/2016 | Tearney | A61B 5/0062 |
| 9,464,883 B2 | 10/2016 | Swanson et al. | |
| 9,513,276 B2 * | 12/2016 | Tearney | A61B 5/0062 |
| 9,615,748 B2 * | 4/2017 | Tearney | A61B 5/0066 |
| 9,664,615 B2 * | 5/2017 | Bouma | G01N 21/474 |
| 9,683,928 B2 | 6/2017 | Swanson | |
| 10,107,616 B2 | 10/2018 | Zhou | |
| 10,132,610 B2 | 11/2018 | Swanson et al. | |
| 10,401,883 B2 | 9/2019 | Swanson et al. | |
| 10,416,288 B2 | 9/2019 | Swanson | |
| 2003/0011779 A1 * | 1/2003 | Swanson | G01N 21/4795 356/479 |
| 2005/0046932 A1 * | 3/2005 | Lange | G02B 21/002 359/368 |
| 2006/0013544 A1 * | 1/2006 | Bouma | G02B 6/02042 385/116 |
| 2006/0164639 A1 * | 7/2006 | Horn | G01J 3/02 356/326 |
| 2006/0187537 A1 | 8/2006 | Huber et al. | |
| 2007/0081236 A1 * | 4/2007 | Tearney | A61B 5/0062 359/390 |
| 2007/0087445 A1 * | 4/2007 | Tearney | A61B 1/043 436/172 |
| 2007/0121196 A1 * | 5/2007 | Tearney | A61B 5/0062 359/333 |
| 2007/0167839 A1 * | 7/2007 | Carver | A61B 5/0068 600/476 |
| 2007/0177152 A1 * | 8/2007 | Tearney | A61B 5/0066 356/477 |
| 2007/0179487 A1 * | 8/2007 | Tearney | A61B 5/0066 606/15 |
| 2007/0233396 A1 * | 10/2007 | Tearney | A61B 5/0062 702/19 |

(56) References Cited

U.S. PATENT DOCUMENTS

| | | | |
|---|---|---|---|
| 2007/0274650 A1* | 11/2007 | Tearney | A61B 1/00082 385/118 |
| 2007/0282403 A1* | 12/2007 | Tearney | A61B 18/24 607/89 |
| 2008/0008478 A1* | 1/2008 | Theis | G02B 23/06 398/182 |
| 2008/0097225 A1* | 4/2008 | Tearney | A61B 18/22 600/478 |
| 2008/0192248 A1* | 8/2008 | Carver | A61B 5/0068 356/301 |
| 2009/0003765 A1* | 1/2009 | Bouma | G02B 6/02042 385/14 |
| 2009/0003789 A1* | 1/2009 | Bouma | G02B 6/02042 385/126 |
| 2009/0022463 A1* | 1/2009 | Bouma | G02B 6/02042 385/126 |
| 2010/0165335 A1* | 7/2010 | Tearney | G01N 21/65 356/301 |
| 2010/0210937 A1* | 8/2010 | Tearney | A61B 5/0066 600/424 |
| 2010/0262115 A1* | 10/2010 | Madiyalakan | A61K 9/0009 604/500 |
| 2010/0296102 A1* | 11/2010 | Galle | G01M 11/3163 356/477 |
| 2010/0329670 A1* | 12/2010 | Essiambre | H04B 10/2581 398/43 |
| 2011/0137178 A1* | 6/2011 | Tearney | A61B 5/0068 600/476 |
| 2011/0144504 A1* | 6/2011 | Tearney | A61B 5/0062 600/476 |
| 2011/0149296 A1* | 6/2011 | Tearney | A61B 5/0062 356/479 |
| 2011/0218404 A1 | 9/2011 | Hirakawa | |
| 2011/0237892 A1* | 9/2011 | Tearney | A61B 5/0062 600/160 |
| 2011/0273718 A1* | 11/2011 | Bouma | G02B 6/02042 356/446 |
| 2012/0093189 A1* | 4/2012 | Fattal | B82Y 20/00 372/50.11 |
| 2012/0099112 A1 | 4/2012 | Alphonse et al. | |
| 2012/0224805 A1* | 9/2012 | Doerr | B29D 11/00663 385/24 |
| 2012/0226118 A1 | 9/2012 | Delbeke et al. | |
| 2012/0302862 A1* | 11/2012 | Yun | A61B 5/0068 600/398 |
| 2013/0066215 A1* | 3/2013 | Tearney | A61B 18/22 600/478 |
| 2013/0068937 A1* | 3/2013 | Ryf | G02B 6/4206 250/227.11 |
| 2013/0077911 A1* | 3/2013 | Doerr | G02B 6/29302 385/11 |
| 2013/0100455 A1* | 4/2013 | Tearney | A61B 5/0062 356/479 |
| 2013/0176571 A1* | 7/2013 | Tearney | A61B 5/0062 356/456 |
| 2013/0209022 A1 | 8/2013 | Doerr | |
| 2013/0215427 A1* | 8/2013 | Bouma | G02B 6/02042 356/446 |
| 2013/0338510 A1* | 12/2013 | Tearney | A61B 5/0066 600/478 |
| 2014/0126902 A1 | 5/2014 | Swanson | |
| 2014/0126990 A1* | 5/2014 | Manes | G11B 15/6835 414/807 |
| 2014/0147079 A1* | 5/2014 | Doerr | G02B 6/262 385/37 |
| 2014/0160488 A1 | 6/2014 | Zhou | |
| 2014/0204604 A1* | 7/2014 | Bouma | G02B 6/02042 362/551 |
| 2014/0376000 A1* | 12/2014 | Swanson | G01B 9/02091 356/479 |
| 2014/0376001 A1* | 12/2014 | Swanson | A61B 5/0066 356/479 |
| 2015/0049339 A1* | 2/2015 | Tearney | A61B 5/0062 356/479 |
| 2015/0085884 A1* | 3/2015 | Fontaine | H04J 14/06 370/542 |
| 2016/0033406 A1* | 2/2016 | Ashrafi | A61B 5/14532 356/432 |
| 2016/0206184 A1* | 7/2016 | Tearney | A61B 5/0062 |
| 2016/0357007 A1* | 12/2016 | Swanson | G02B 23/26 |
| 2017/0143196 A1 | 5/2017 | Liang et al. | |
| 2017/0205253 A1 | 7/2017 | Handerek | |
| 2017/0360297 A1* | 12/2017 | Yun | A61B 3/1025 |

FOREIGN PATENT DOCUMENTS

| | | | | |
|---|---|---|---|---|
| EP | 0971626 A1 | * | 1/2000 | ......... A61B 1/00096 |
| EP | 0981733 B1 | | 11/2004 | |
| EP | 0883793 B1 | * | 11/2007 | ......... A61B 1/00096 |
| EP | 1839375 B1 | | 4/2014 | |
| JP | 2002214127 A | * | 7/2002 | ......... A61B 1/00096 |
| JP | 2004105708 A | * | 4/2004 | ......... A61B 1/00096 |
| WO | WO 9008433 A1 | * | 7/1990 | ......... H04B 10/118 |
| WO | WO 9105414 A1 | * | 4/1991 | ............ H04B 10/11 |
| WO | WO 9533970 A1 | * | 12/1995 | ......... A61B 1/00183 |
| WO | WO 9533971 A1 | * | 12/1995 | ......... A61B 1/00183 |
| WO | WO 9701167 A1 | * | 1/1997 | ........... A61B 5/0066 |
| WO | WO 9732182 A1 | * | 9/1997 | ......... A61B 1/00096 |
| WO | WO 9835203 A2 | * | 8/1998 | ......... A61B 1/00183 |
| WO | WO 9838907 A1 | * | 9/1998 | ......... A61B 1/00096 |
| WO | WO 0042906 A3 | * | 1/2001 | ......... A61B 1/00172 |
| WO | 2012088361 | | 6/2012 | |

OTHER PUBLICATIONS

Lemire-Renaud et al., "Double-clad fiber with a tapered end for confocal endomicroscopy," Biomed. Opt. Express 2, 2961-2972 (2011).*

Leon-Saval et al., "Mode-selective photonic lanterns for space-division multiplexing," Opt. Express 22, 1036-1044 (2014).*

Madore et al., "Asymmetric double-clad fiber couplers for endoscopy," Opt. Lett. 38, 4514-4517 (2013).*

Fontaine et al., "Few-Mode Fiber Wavelength Selective Switch with Spatial-Diversity and Reduced-Steering Angle," in Optical Fiber Communication Conference, OSA Technical Digest (online) (Optical Society of America, 2014), paper Th4A.7.*

Marom et al., "Wavelength-selective switch with direct few mode fiber integration," Opt. Express 23, 5723-5737 (2015).*

Oh et al., Optical fibers for high-resolution in vivo microendoscopic fluorescence imaging, Optical Fiber Technology, vol. 19, Issue 6, Part B,2013,pp. 760-771.*

Yu et al., Experimental Characterization of Rayleigh Backscattering in Few-Mode Fiber Using All-Fiber Photonic Lanterns, in Asia Communications and Photonics Conference 2015, C. Lu, J. Luo, Y. Ji, K. Kitayama, H. Tam, K. Xu, P. Ghiggino, and N. Wada, eds., OSA Technical Digest (online) (Optical Society of America, 2015), paper AM2B.4.*

Francois Parnet, Julien Fade, and Mehdi Alouini, "Orthogonality breaking through few-mode optical fiber," Appl. Opt. 55, 2508-2520 (2016) (Year: 2016).*

Reck et al., Experimental realization of any discrete unitary operator, Phys. Rev. Lett. 73, 58—Published Jul. 4, 1994 (Year: 1994).*

Weng et al., Single-end simultaneous temperature and strain sensing techniques based on Brillouin optical time domain reflectometry in few-mode fibers Opt. Express 23, 9024; (Year: 2015).*

Fujimoto et al., Optical Coherence Tomography: An Emerging Technology for Biomedical Imaging and Optical Biopsy, Neoplasia, V. 2, Nos. 1-2, 2000 (Year: 2000).*

Huang et al., Optical Coherence Tomography, Science, Nov. 22, 1991; 254(5035): 1178-1181 (Year: 1991).*

Ozdur et al., Free-space to single-mode collection efficiency enhancement using photonic lanterns, Optics Letters, V. 38, N. 18, 2013 (Year: 2013).*

Ozdur et al., Photonic-lantern-based coherent LIDAR system, Optics Express, V. 23, N. 4., 2015 (Year: 2015).*

(56) References Cited

OTHER PUBLICATIONS

Qui et al., Exploiting few mode-fibers for optical time-stretch confocal microscopy in the short near-infrared window, Optice Express, V. 20, N. 22, 2012 (Year: 2012).*
Schmitt, Joseph, Optical Coherence Tomography (OCT): A Review, IEEE Journal of Selected Topics in Quantum Electronics, vol. 5, No. 4, Jul./Aug. 1999 (Year: 1999).*
Yu, Siyuan, Manipulating Optical Vortices Using Photonic Integration, 2015, AAPPS Bulletin, V. 25, N. 2. (Year: 2015).*
Kevin Gourley, Ilya Golu, Brahim Chebbi, "First experimental demonstration of a Fresnel Axicon", Proceedings of the SPIE, doi:10.1117/12.807162, Jun. 18, 2008.
Oto Brzobohatý, TomášČižmár, and Pavel Zemánek, "High quality quasi-Bessel beam generated by round-tip axicon", Optics Express, vol. 16, No. 17, 2008.
"Tapered Mode Multiplexers for Single Mode to Multi Mode Fibre Mode Transitions", S. Yerolatsitis, I. Gris-Sánchez, T. A. Birks, Proceedings of the Optical Fiber Communications Conference, Paper w3B.4, 2015.
"Six mode selective fiber optic spatial multiplexer", A. M. Velazquez-Benitez, J. C. Alvarado, G. Lopez-Galmiche, J. E. Antonio-Lopez, J. Hernández-Cordero, J. Sanchez-Mondragon, P. Sillard, C. M. Okonkwo, and R. Amezcua-Correa, Optics Letters, vol. 40, No. 8, Apr. 15, 2015.
"Selective Excitation of High Order Modes in Few Mode Fibres Using Optical Microfibres", Bernard Oduro, Rand Ismaeel, Timothy Lee and Gilberto Brambilla, Proceedings of the Optical Fiber Communications Conference, Paper M3D.5, 2015.
"Recent Progress in the Development of Few Mode Fiber Amplifiers", S. U. Alam*, Y. Jung, Q. Kang, F. Poletti, J.K. Sahu and D. J. Richardson, Proceedings of the Optical Fiber Communications Conference, Paper Tu3C.1, 2015.
"Photonic-Lantern-Based Mode Multiplexers for Few-Mode-Fiber Transmission", R. Ryf1, N. K. Fontaine1, M. Montoliu, S. Randel1, B. Ercan, H. Chen, S. Chandrasekhar, A. H. Gnauck, S. G. Leon-Saval, J. Bland-Hawthorn, J. R. Salazar-Gil, Y. Sun, R. Lingle, Jr., Proceedings of the Optical Fiber Communications Conference, Paper W4J.2., 2015.
"Mode-selective photonic lanterns for space division multiplexing", Sergio G. Leon-Saval, Nicolas K. Fontaine, Joel R. Salazar-Gil, Burcu Ercan, Roland Ryf, and Joss Bland-Hawthorn, Optics Express, vol. 22, No. 1 Jan. 13, 2014.
"Design Constraints of Photonic-Lantern Spatial Multiplexer Based on Laser-Inscribed 3-D Waveguide Technology", Haoshuo Chen, Nicolas K. Fontaine, Roland Ryf, Binbin Guan, S. J. Ben Yoo, and Ton (A. M. J.) Koonen, Journal of Lightwave Technology, vol. 33, No. 6, Mar. 15, 2015.
"Compact spatial multiplexers for mode division multiplexing", Haoshuo Chen, Roy van Uden, Chigo Okonkwo, and Ton Koonen, Optics Express, vol. 22, No. 26, Dec. 26 2014.
Optical coherence tomography system mass producible on a silicon photonic chip, Simon Schneider, Matthias Lauermann, Philipp-Immanuel Dietrich, Claudius Weimann, Wolfgang Freude, and Christian Koos, Optics Express, vol. 24, No. 2, Jan. 2016.
"Miniature Optical Coherence Tomography System Based on Silicon Photonics", Eduardo Margallo-Balb'as, Gregory Pandraud and Patrick J. French, SPIE 2Proceedings, vol. 6847 (2008).
Christopher R. Doerr and Lawrence L. Buhl, "Circular Grating Coupler for Creating Focused Azimuthally and Radially Polarized Beams", Optics Letters, vol. 36, No. 7, Apr. 1, 2011.
"Terabit-Scale Orbital Angular Momentum Mode Division Multiplexing in Fibers", Nenad Bozinovic, Yang Yue, Yongxiong Ren, Moshe Tur, Poul Kristensen, Hao Huang, Alan E. Willner, Siddharth Ramachandran, Science Magazine, vol. 340 Jun. 28, 2013.
Hitzenberger, Christoph K., et at., In Vivo Intraocular Ranging by Wavelength Tuning Interferometry, SPIE, pp. 47-51, vol. 3251, retrieved from: http://proceedings.spiedigitallibrary.org/ on Sep. 24, 2013.

Guan, et al. Mode-Group-Selective Photonic Lantern based on Integrated 3D Devices Fabricated by Ultrafst Laser Inscription, 3 pages.
Warren L. Stutzman and Gary A. Thiele, "Antenna Theory and Design", John Wiley & Sons, ISBN 0-471-04458-X, 1981. Textbook.
Y. Zhao, Z. Chen, C. Saxer, S. Xiang, J.F. de Bear, and J.S. Nelson, "Phase-resolved optical coherence tomography and optical Doppler tomography for imaging blood flow in human skin with fast scanning speed and high velocity sensitivity," Opt. Lett. 25(2), 114-116 (2000).
W. Choi, B. Potsaid, V. Jayaraman, B. Baumann, I. Grulkowski, J. J. Liu, C. D. Lu, A. E. Cable, D. Huang, J. S. Duker, and J. G. Fujimoto, "Phase sensitive swept-source optical coherence tomography imaging of the human retina with a vertical cavity surface-emiting laser light source," Opt. Lett. 38(3), 338-340 (2013).
Youxin Mao, Costel Flueraru, Shoude Chang, Dan P. Popescu, Michael G. Sowa, "Performance analysis of a swept-source optical coherence tomography system with a quadrature interferometer and optical amplification", Optics Communications, vol. 284, Issues 10-11, May 15, 2011.
C. M. Eigenwillig, B. R. Biederman, G. Palte, and R. Huber, "K-space linear Fourier domain mode locked laser and applications for optical coherence tomography," Optics Express 16(12), 8916-8937 (2008).
"Scanning fiber angle-resolved low coherence interferometry", Yizheng Zhu, Neil G. Terry, and Adam Wax, Optics Letters, vol. 34, No. 20, 2009.
"Size and shape determination of spheroidal scatters using two-dimensional angle resolved scattering", Michael Giacomelli, Yizheng, Zhu, John Lee, Adam Wax, Optics Express, vol. 18, No. 14, 2010.
Hulme, J. C. et al., "Fully integrated hybrid silicon free-space beam steering source with 32 channel phased array" International Society for Optics and Photonics (SPIE PW), San Fransisco, CA Feb. 1-6, 2014, pp. 898907-1-898907-15.
G. Yurtsever, B. Pova2ay, A. Alex, B. Zabihian, W. Drexler, and R. Baets, "Photonic integrated Mach-Zehnder interferometer with an on-chip reference arm for optical coherence tomography," Biomed. Opt. Express 5(4), 1050-1061 (2014).
G. Yurtsever, N. Weiss, J. Kalkman, T. G. van Leeuwen, and R. Baets, "Ultra-compact silicon photonic integrated interferometer for swept-source optical coherence tomography," Opt. Lett. 39(17), 5228-5231 (2014).
B. I. Akca, B. Povazay, A. Alex, K. Worhoff, R. M. de Ridder, W. Drexler, and M. Pallnau, "Miniature spectrometer and beam splitter for an optical coherence tomography on a silicon chip", Optics Express, vol. 31, No. 14, Jul. 3, 2014.
Kyle Preston, Arthur Nitkowski, Nicolás Sherwood-Droz, Andrew Berkeley, Bradley S. Schmid, and Arsen R. Hajian, 'OCTANE: Optical Coherence Tomography Advanced Nanophotonic Engine, CLEO 2013 Technical Digest, Paper AW31.5, Jun. 9-14, 2013.
Daniel Neill, Luke Stewart, Huiping Li, Tom Killin, Fan Chen, Steve Frisken, Glenn Baxter, Simon Poole, "Compact polarization diverse receiver for biomedical imaging Applications", SPIE Proceedings, vol. 7891, Jan. 22, 2011.
Arthur Nitkowski, Kyle Preston, Nicolás Sherwood-Droz, Andrew Berkeley, Bradford B. Behr, Bradley S. Schmidt, and Arsen R. Hajian, "Nano Spectrometer for Optical Coherence Tomography", Imaging and Applied Optics Conference, Paper AM1B.3, (2013).
B. Imran Akca, "Spectral-Domain Optical Coherence Tomography on a Silicon Chip", PhD Thesis. University of Twente, (2012).
D. Culemann, A. Knuettel, and E. Voges, "Integrated optical sensor in glass for optical coherence tomography," IEEE J. Sel. Topics Quantum Electron., vol. 6, No. 5, pp. 730-734, Oct. 2000.
E. Margallo-Balbas,M. Geljon, G. Pandraud, and P. J. French, "Miniature 10 kHz thermo-optic delay line in silicon," Opt. Lett., vol. 35, No. 23, pp. 4027-4029, Dec. 2010.
Kerstin Worhoff, Nur Ismail, B. Imran Akca, Markus Pollnau, and Rene M. De Ridder, "Silicon Oxynitride Technology for Integrated Optical Solutions in Biomedical Applications", In: 13th International Conference on Transparent Optical Networks 2011, Jun. 26-30, 2011, Stockholm, Sweden.

(56) References Cited

OTHER PUBLICATIONS

G. Yurtsever, P. Duman, W. Bogaerts, and R. Baets, "Integrated photonic circuit in silicon on insulator for Fourier domain optical coherence tomography," in Proc. SPIE, Opt. Coherence Tomography Coherence Domain Opt. Methods Blamed. XIV, vol. 7554, San Francisco, CA, 2010, pp. 1-5.
V. D. Nguyen, N. Ismail, F. Sun, K. Worhoff, T. G. van Leeuwen, and J. Kalkman, "SiON integrated optics elliptic couplers for Fizeau-based optical coherence tomography," IEEE J. Lightw. Technol., vol. 28, No. 19, pp. 2836-2842, Sep. 2010.
Haitham Omran, Yasser M. Sabry, Mohamed Sadek, Khaled Hassan, Mohamed Y. Shalaby and Diaa Khalil, "Deeply-Etched Optical MEMS Tunable Filter for Swept Laser Source Applications", IEEE Photonics Technology Letters. vol. 26, No. 1, Jan. 2014.
Firooz Aflatouni, Behrooz Abiri, Angad Rekhi, and Ali Hajimiri, "Nanophotonic coherent imager", Optics Express, vol. 23, No. 4, doi: 10.1364/OE23.005117, 2015.
Gyeong Cheol Park, Weigi Xue, Elizaveta Semenova, Kresten Yvind, Jesper Mork, and Il-Sug Chung, "III-V/SOI Vertical Cavity Laser with In-plane Output into a Si Waveguide", Paper W2A.17, Proceedings of the Optical Fiber Communication Conference, 2015.
K. Worhoff, C. G. H. Roeloffzen, R. M. de Ridder, A. Driessen, and P. V. Lambeck, "Design and application of compact and highly tolerant polarization-independent waveguides," IEEE J. Lightw. Technol., vol. 25, No. 5, pp. 1276-1282, May 2007.
S. K. Selvaraja, W. Bogaerts, P. Absil, D. Van Thourhout, and R. Baets, "Record low-loss hybrid rib/wire waveguides for silicon photonic circuits," Group IV Photonics (2010).
D. Vermeulen, S. Selvaraja, P. Verheyen, G. Lepage, W. Bogaerts, P. Absil, D. Van Thourhout, and G. Roelkens, "High-efficiency fiber-to-chip grating couplers realized using an advanced CMOS-compatible silicon-on-insulator platform," Opt. Express 18(17), 18278-18283 (2010).
D. Vermeulen, S. Selvaraja, P. Verheyen, P. Absil, W. Bogaerts, D. Van Thourhout, and G. Roelkens, "Silicon-on-insulator polarization rotator based on a symmetry breaking silicon overlay," IEEE Photonics Technol. Lett. 24(5), 482 (2012).
A. Mekis, A. Dodabalapur, R. Slusher, and J. D. Joannopoulos, "Two-dimensional photonic crystal couplers for unidirectional light output," Opt. Lett. 25(13), 942-944 (2000).
L. Chen, C. R. Doerr, L. Buhl, Y. Baeyens, and R. A. Aroca, "Monolithically integrated 40-wavelength demultiplexer and photodetector array on silicon," IEEE Photonics Technol. Lett. 23(13), 869-871 (2011).
C. R. Doerr, L. Chen, D. Vermeulen, T. Nielsen, S. Azemati, S. Stulz, G. McBrien, X.-M. Xu, B. Mikkelsen, M. Givehchi, C. Rasmussen, and S. Y. Park, "Single-chip silicon photonics 100-Gb/s coherent transceiver," in Optical Fiber Communication Conference, (Optical Society of America, 2014), Th5C. 1.
M. Izutsu, S. Shikama, and T. Sueta, "Integrated optical SSB modulator/frequency shifter," IEEE J. Quant. Electron., vol. 2, No. 11, pp. 2225-2227, 1981.
D. Taillaert, H. Chong, P. I. Borel, L. H. Frandsen, R. M. D. L. Rue, and R. Baets, "A compact two-dimensional grating coupler used as a polarization splitter", IEEE Photon. Tech. Lett., vol. 15, pp. 1249-1251, 2003.
R. Nagarajan and Others, "10 Channel, 100Gbit/s per Channel, Dual Polarization, Coherent QPSK, Monolithic InP Receiver Photonic Integrated Circuit", Optical Fiber Communication Conference Proceedings, p. OML7, 2011.
N. Dupuis, C. R. Doerr, L. Zhang, L. Chen, N. J. Sauer, P. Dong, L. L. Buhl, and D. Ahn, "InP-based comb generator for optical OFDM," J. Lightw. Technol., 2011.
S. Chandrasekhar and Xiang Liu, "Enabling Components for Future High-Speed Coherent Communication Systems", Optical Fiber Communication Conference Tutorial, 2011.
G. Roelkens, D. Vermeulen, S. Selvaraja, Student Member, IEEE, R. Halir, W. Bogaerts, Member, IEEE, and D. Van Thourhout, "Grating-Based Optical Fiber Interfaces for Silicon-on-Insulator Photonic Integrated Circuits", IEEE Journal of Selected Topics in Quantum Electronics, vol. 17, No. 3, May/Jun. 2011.
Attila Mekis, Steffen Gloeckner, Gianlorenzo Masini, Adithyaram Narasimha, Member, IEEE, Thierry Pinguet, Subal Sahni, and Peter De Dobbelaere,"A Grating-Coupler-Enabled Cmos Photonics Platform". IEEE Journal of Selected Topics in Quantum Electronics, vol. 17, Issue 3, May/Jun. 2011.
Neil NA, Harel Frish, I-Wei Hsieh, Oshrit Harel, Roshan George, Assia Barkai, and Haisheng Rong, "Efficient broadband silicon-on-insulator grating coupler with low backreflection", Optics Letters, vol. 36, No. 11, Jun. 1, 2011.
Wissem Sfar Zaoui, Maria Felix Rosa, Wolfgang Vogel, Manfred Berroth Jörg Butschke, and Florian Letzkus, "Cost-affective CMOS-compatible grating couplers with backside metal mirror and 69% coupling efficiency", Optics Express, vol. 20, No. 26, Dec. 10, 2012.
Vilson R. Almeida, Roberto R. Panepucci, and Michal Lipson, "Nanotaper for compact mode conversion", Optics Letters, vol. 28, No. 15, Aug. 1, 2003.
Anatol Khilo, Miloš A. Popović, Mohammad Araghchini, and Franz X. Kärtner, "Efficient planar fiber-to-chip coupler based on two-stage adiabatic evolution", Optics Express, vol. 18, No. 15, Jul. 19, 2010.
Long Chen, Christopher R. Doerr, Young-Kai Chen, and Tsung-Yang Liow, "Low-Loss and Broadband Cantilever Couplers Between Standard Cleaved Fibers and High-Index-Contrast Si3N4 or Si Waveguides", IEEE Photonics Technology Letters, vol. 22, No. 23, Dec. 1, 2010.
Alan Y. Liu, Chong Zhang, Justin Norman, Andrew Snyder, Dmitri Lubyshev,Joel M. Fastenau, Amy W. K. Liu, Arthur C. Gossard, and John E. Bowers, "High performance continuous wave 1.3 Im quantum dot lasers on silicon", Applied Physics Letters,104, 041104 (2014.
Jie Sun, Erman Timurdogan, Ami Yaacobi, Zhan Su, Ehsan Shah Hosseini, David B. Cole, and Michael R. Watts, "Large-Scale Silicon Photonic Circuits for Optical Phased Arrays", IEEE Journal of Selected Topics in Quantum Electronics, vol. 20, No. 4, Jul./Aug. 2014.
Jie Sun, Ehsan Shah Hosseini, Ami Yaacobi, David B. Cole, Gerald Leake, Douglas Coolbaugh, and Micheael R. Watts, "Two-dimensional apodized silicon photonic phased arrays", Optics Letters, vol. 39, No. 2, Jan. 15, 2014.
C. T. DeRose, R. D. Kekatpure, D. C. Trotter, A. Starbuck. J. R. Wendt, A. Yaacobi, M. R. Watts, U. Chettiar, N. Engheta, and P. S. Davids, "Electronically controlled optical beam-steering by an active phased array of metallic nanoantennas", Optics Express, vol. 21, No. 4, Feb. 25, 2013.
Jie Sun, Erman Timurdogan, Ami Yaacobi, Ehsan Shah Hosseini, and Michel R. Watts, "Large-scale nanophotonic phased array", Nature, vol. 493, Jan. 10, 2013.
Ami Yaacobi Erman Timurdogan, and Michael R. Walls, "Vertical emitting aperture nanoantennas", Optics Letters, vol. 37, No. 9, May 1, 2012.
J. K. Doylend, M. J. R. Heck, J. T. Bovington, J. D. Peters, L. A. Coldre, and J. E. Bowers, "Two-dimensional free-space beam steering with an optical phased array of silicon-on-insulator", Optics Express, vol. 19, No. 22, Oct. 24, 2011.
Karel Van Acoleyen, Hendrick Rogier, and Roel Baets, "Two-dimensional optical phased array antenna on silicon-on-insulator", Optics Express, vol. 18, No. 13, Jun. 21, 2010.
James A. Burns, Brian F. Aull, Chenson K. Chen, Chang-Lee Chen, Craig L. Keast, Jeffrey M. Knecht, Vyshanavi Suntharalingam, Keith Warner, Peter W. Wyatt, and Donna-Ruth W. Yost, "A Wafer-Scale 3-D Circuit Integration Technology", IEEE Transactions on Electronic Devices, vol. 53, No. 10, Oct. 2006.
Dirk Lorenser, C. Christian Singe, Andrea Curatolo, and David D. Sampson, "Energy-efficient low-Fresnel-number Bessel beams and their application in optical coherence tomography", Optics Letters, vol. 39, No. 3, Feb. 1, 2014.
Niklas Weber, Dominik Spether, Andreas Seifert, and Hans Zappe, "Highly compact imaging using Bessel beams generated by ultraminiaturized multi-micro-axicon systems", Journal of Optical Society of America A. vol. 29, No. 5, May 2012.

(56) References Cited

OTHER PUBLICATIONS

Z. Xie, B. Armbruster, and T. Grosjean, "Axicon on a gradient index lens (AXIGRIN)): integrated otial bench for Bessel beam generation from a point-like source", Applied Optics, vol. 53, Issue 26, (2014).
G.S. Sokolovskii, V.V. Dudelev, S.N. Losev, K.K. Soboleva, A.G. Deryagin, K.A. Fedorovac, V.I. Kuchinskii, W. Sibbett, E.U. Rafailov, "Bessel beams from semiconductor light sources", Progress in Quantum Electronics, vol. 38, No. 4, Jul. 2014.
F. Merola ; S. Coppola ; V. Vespini ; S. Galli ; P. Ferraro ; D. Balduzzi ; A. Galli ; R. Puglisi, "Fabrication and test of polymeric microaxicons", Proceedings of the SPIE, doi:10.1117/12.922572, Jun. 1, 1012.
Paul Steinvurzel, Khwanchai Tantiwanichapan, Masao Goto, and Siddharth Ramachandran, "Fiber-based Bessel beams with controllable diffraction-resistant distance", Optics Letters, vol. 36, No. 23, 2011.
Cedric Blatter ; Branislav Grajciar ; Christoph M. Eigenwillig; Wolfgang Wieser; Benjamin R. Biedermann; Robert Huber; Rainer A. Leitgeb, "High-speed functional OCT with self-reconstructive Bessel illumination at 1300 nm", Proceedings of the SPIE, doi:10.1117/12.889669, Jun. 1, 2011.
D. Huang, E. A. Swanson, C. P. Lin, J. S. Schuman, W. G. Stinson, W. Chang, M. R. Hee, T. Flotte, K. Gregory, C. A. Puliafito and J. G. Fujimoto, "Optical coherence tomography," Science 254(5035), 1178-1181 (1991).
R. Leitgeb, C. Hitzenberger, and A. Fercher, "Performance of fourier domain vs. time domain optical coherence tomography," Opt. Express 11(8), 889-894 (2003).
J. F. de Boer, B. Cense, B. H. Park, M. C. Pierce, G. J. Tearney, and B. E. Bouma, "Improved signal-to-noise ratio in spectral-domain compared with time-domain optical coherence tomography," Opt. Lett. 28(21), 2067-2069 (2003).
M. Choma, M. Sarunic, C. Yang, and J. Izall, "Sensitivity advantage of swept source and Fourier domain optical coherence tomography," Opt. Express 11(18), 2183-2189 (2003).
M. Wojtkowski, A. Kowalczyk, R. Leitgeb, and A. F. Fercher, "Full range complex spectral optical coherence tomography technique in eye imaging," Opt. Lett. 27(16), 1415-1417 (2002).
A. F. Fercher, C. K. Hitzenberger, G. Kamp, and S. Y. El-Zaiat, "Measurement of intraocular distances by backscattering spectral interferometry," Opt. Commun. 117(1), 43-48 (1995).
S. R. Chinn, E. A. Swanson, and J. G. Fujimoto, "Optical coherence tomography using a frequency-tunable optical source," Opt. Lett. 22(5), 340-342 (1997).
S. Yun, G. Tearney, J. de Boer, N. Iftimia, and B. Bouma, "High-speed optical frequency-domain imaging," Opt. Express 11(22), 2953-2963 (2003).
R. Huber, M. Wojtkowski, and J. G. Fujimoto, "Fourier Domain Mode Locking (FDML): A new laser operating regime and applications for optical coherence tomography," Opt. Express 14(8), 3225-3237 (2006).
R. Huber, D. C. Adler, and J. G. Fujimoto, "Buffered Fourier domain mode locking: unidirectional swept laser sources for optical coherence tomography imaging at 370,000 lines/s," Opt. Lett. 31(20), 2975-2977 (2006).
B. Potsaid, V. Jayaraman, J. G. Fujimoto, J. Jiang, P. J. Heim, and A. E. Cable, "MEMS tunable VCSEL light source for ultrahigh speed 60kHz-1MHz axial scan rate and long range centimeter class OCT imaging," in SPIE BiOS, (International Society for Optics and Photonics), (2012).
V. Jayaraman, . G. D. Cole, M. Robertson, A. Uddin, and A. Cable, "High-sweep-rate 1310 nm MEMS-VCSEL with 150 nm continuous tuning range," Electron. Lett. 48(14), 867-869 (2012).
W. Wieser, W. Draxinger, T. Klein, S. Karpf, T. Pfeiffer, and R. Huber, "High definition live 3D-OCT in vivo: design and elaluation of a 4D OCT engine with 1 GVoxells," Mimed. Opt. Express 5(9), 2963-2977 (2014).

M.V. Sarunic, B.E. Applegate, and J.Izaft, "Real-Time Quadrature Projection Complex Conjugate Resolved Fourier Domain Optical Coherence Tomography," Optics Letters, vol. 31, No. 16, Aug. 15, 2006.
R. K. Wang, S. L. Jacques, Z. Ma, S. Hurst, S. R. Hanson, and A. Gruber, "Three dimensional optical angiography," Opt. Express 15(7), 4083-4097 (2007).
Y. Jia, O. Tan, J. Tokayer, B. Potsaid, Y. Wang, J. J. Liu, M. F. Kraus, H. Subhash, J. G. Fujimoto, J. Hornegger, and D. Huang, "Split-spectrum amplitude-decorrelation angiography with optical coherence tomography," Opt. Express 20 (4), 4710-4725 (2012).
S. Makita, Y. Hong, M. Yamanari, T. Yatagai, and Y. Yasuno, "Optical coherence angiography," Opt. Express 14(17), 7821-7840 (2006).
S. Yazdanfar, M. Kulkarni, and J. Izatt, "High resolution imaging of in vivo cardiac dynamics using color Doppler optical coherence tomography," Opt. Express 1(13), 424-431 (1997).
B. Vakoc, S. Yun, J. de Boer, G. Tearney, and B. Bouma, "Phase-resolved optical frequency domain imaging," Opt. Express 13(14), 5483-5493 (2005).
M. R. Hee, E. A. Swanson, J. G. Fujimoto, and D. Huang, "Polarization-sensitive low-coherence reflectometer for birefringence characterization and ranging," J. Opt. Soc. Am. B 9(6), 903-908 (1992).
J. F. de Boer and T. E. Milner, "Review of polarization sensitive optical coherence tomography and Stokes vector determination," J. Biomed. Opt. 7(3), 359-371 (2002).
M. Pircher, C. K. Hitzenberger, and U. Schmidt-Erfurth, "Polarization sensitive optical coherence tomography in the human eye," Prog. Retin. Eye. Res. 30(6), 431-451 (2011).
S. K. Nadkarni, M. C. Pierce, B. H. Park, J. F. de Boer, P. Whittaker, B. E. Bouma, J. E. Bressner, E. Halpern, S. L. Houser, and G. J. Teamey, "Measurement of Collagen and Smooth Muscle Cell Content in Atherosclerotic Plaques Using Polarization-Sensitive Optical Coherence Tomography," J. Am. Coll. Cardiol. 49(13), 1474-1481 (2007).
B. R. Biedermann, W. Wieser, C. M. Eigenwillig, T. Klein, and R. Huber, "Dispersion, coherence and noise of Fourier domain mode locked lasers," Opt. Express 17(12), 9947-9961 (2009).
M. Sarunic, M. A. Choma, C. Yang, and J. A. Izatt, "Instantaneous complex conjugate resolved spectral domain and swept-source OCT using 3x3 fiber couplers," Opt. Express 13(3), 957-967 (2005).
R. K. Wang, "In vivo full range complex Fourier domain optical coherence tomography," Appl. Phys. Left. 90(5), 054103 (2007).
M. Yamanari, S. Makita, Y. Lim, and Y. Yasuno, "Full-range polarization-sensitive swept-source optical coherence tomography by simultaneous transversal and spectral modulation," Opt. Express 18(13), 13964-13980 (2010).
S. Yun, G. Teamey, J. de Boer, and B. E. Bouma, "Removing the depth-degeneracy in optical frequency domain imaging with frequency shifting," Opt. Express 12(20), 4822-4828 (2004).
B. J. Vakoc, S. H. Yun, G. J. Tearney, and B. E. Bouma, "Elimination of depth degeneracy in optical frequency-domain imaging through polarization-based optical demodulation," Opt. Lett. 31(3), 362-364 (2006).
M. Siddiqui, S. Tozburun, E. Z. Zhang, and B. J. Vakoc, "Compensation of spectral and RF errors in swept-source OCT for high extinction complex demodulation," Opt. Express 23, 5508-5520 (2015).
K.-S. Lee, P. Meemon, W. Dallas, K. Hsu, and J. P. Rolland, "Dual detection full range frequency domain optical coherence tomography," Opt. Lett. 35(7), 1058-1060 (2010).
B. Hofer, B. Považay, B. Hermann, A. Unterhuber, G. Matz, and W. Drexler, "Dispersion encoded full range frequency domain optical coherence tomography," Opt. Express 17(1), 7-24 (2009).
T.-H. Tsai, B. Potsaid, Y. K Tao, V. Jayaraman, J. Jiang, P. J. S. Heim, M. F. Kraus, C. Zhou, J. Homegger, H. Mashimo, A. E. Cable, and J. G. Fujimoto, "Ultrahigh speed endoscopic optical coherence tomography using micromotor imaging catheter and VCSEL technology," Biomed. Opt. Express 4(7), 1119-1132 (2013).
B. Baumann, W. Choi, B. Potsaid, D. Huang, J. S. Duker, and J. G. Fujimoto, "Swept source Fourier domain polarization sensitive optical coherence tomography with a passive polarization delay unit," Opt. Express 20(9), 10229-10241 (2012).

(56) References Cited

OTHER PUBLICATIONS

Z. Wang, H.-C. Lee, O. O. Ahsen, B. Lee, W. Choi, B. Potsaid, J. Liu, V. Jayaraman, A. Cable, M. F. Kraus, K. Liang, J. Homegger, and J. G. Fujimoto, "Depth-encoded all-fiber swept source polarization sensitive OCT," Biomed. Opt. Express 5(9), 2931-2949 (2014).

B. H.Park, M. C. Pierce, B. Cense, and J. F. de Boer, "Jones matrix analysis for a polarization-sensitive optical coherencetomography system using fiber-optic components," Opt. Lett. 29(21), 2512-2514 (2004).

H. Pahlevaninezhad, A. Lee, L Cahill, S. Lam, C. MacAulay, and P. Lane, "Fiber-Based Polarization Diversity Detection for Polarization-Sensitive Optical Coherence Tomography," Photonics 1(4), 283-295 (2014).

T. S. Ralston, D. L. Marks, P. S. Carney, and S. A. Boppart, "Interferometric synthetic aperture microscopy," Nat. Phys. 3(2), 129-134 (2007).

U. Morgner, W. Drexler, F. Kärtner, X. Li, C. Pitris, E. Ippen, and J. G. Fujimoto, "Spectroscopic optical coherence tomography," Opt. Lett. 25(2), 111-113 (2000).

R. Huber, M. Wojtkowski, J. G. Fujimoto, J. Y. Jiang, and A. E. Cable, "Three-dimensional and C-mode OCT imaging with a compact, frequency swept laser source at 1300 nm," Optics Express 13(26), 10523-10538 (2005).

R. Huber, M. Wojtkowski, K. Taira, J. G. Fujimoto, and K. Hsu, "Amplified, frequency swept lasers for frequency domain reflectometry and OCT imaging: design and scaling principles," Optics Express 13(9), 3513-3528 (2005).

B. Potsaid, I. Gorczynska, V. J. Srinivasan, Y. L. Chen, J. Jiang, A. Cable, and J. G. Fujimoto, "Ultrahigh speed spectral / Fourier domain OCT ophthalmic imaging at 70,000 to 312,500 axial scans per second," Optics Express 16 (19), 15149-15169 (2008).

V. D. Nguyen, B. I. Akca, K. Wörhoff, R. M. De Ridder, M. Pollnau, T. G. van Leeuwen, and J. Kalkman, "Spectral domain optical coherence tomography imaging with an integrated optics spectrometer," Opt. Lett. 36, 1293-1295 (2011.

Jiefeng Xi, Li Huo, Jiasong Li and Xingde Li, "Generic real-time uniform K-space sampling method for high-speed swept-Source optical coherence tomography", Optics Express, vol. 18, No. 9, Apr. 26, 2010.

V. Jayaraman, G.D. Cole, M. Robertson, C. Burgner, D. John, A. Uddin and A. Cable, "Rapidly swept, ultra-widely-tunable 1060 nm MEMS-VCSELs", Electronics Letters, Oct. 11, 2012 vol. 48 No. 21.

G. J. Teamey, R. H. Webb, and B. E. Bouma, "Spectrally Encoded Confocal Microscopy", Optics Letters, vol. 23, No. 15, Aug. 1, 1998.

Chen D. Lu, Martin F. Kraus, Benjamin Potsaid, Jonathan J. Liu, WooJhon Choi, Vijaysekhar Jayaraman, Alex E. Cable, Joachim Hornegger, Jay S. Duker and James G. Fujimoto, "Handheld ultrahigh speed swept source optical coherence tomography instrument using a MEMs scanning mirror", Biomedical Optics Express, vol. 5, No. 1, Jan. 1, 2014.

V. D. Nguyen, N. Weiss, W. Beeker, M. Hoekman, A. Leinse, R. G. Heideman, T. G. van Leeuwen, and J. Kalkman, "Integrated-optics-based swept-source optical coherence tomography," Opt. Lett. 37(23), 4820-4822 (2012).

B. I. Akca, V. Nguyen, J. Kalkman, N. Ismail, G. Sengo, S. Fei, A. Driessen, T. G. van Leeuwen, M. Pollnau, K. Worhoff, and R. M. de Ridder, "Toward Spectral-Domain Optical Coherence Tomography on a Chip," IEEE J. Sel. Top. Quantum Electron. 18(3), 1223-1233 (2012).

James G. Fujimoto, Eric Swanson, Robert Huber, European Inventor Award 2017, Jun. 15, 2017, 3 pages. PRWeb.

C. Boudoux, et al., Rapid wavelength-swept spectrally encoded confocal microscopy, Optics Express, Oct. 3, 2005, pp. 8214-8221, vol. 13, No. 20, OSA.

Dongyao Cui, et al., Multifiber angular compounding optical coherence tomography for speckle reduction, Optics Letter, Jan. 1, 2017, pp. 125-128, vol. 42, No. 1, Optical Society of America.

Daniel J. Fechtig, et al., Line-field parallel swept source MHz OCT for structural and functional retinal imaging, Biomedical Optics Express, Mar. 1, 2015, pp. 716-735, vol. 6, No. 3, OSA.

Simon Lemire-Renaud, et al., Double-clad fiber coupler for endoscopy, Optics Express, May 10, 2020, 9755-9764, vol. 18, No. 10, OSA.

Florence Rossant, et al., Highlighting directional reflectance properties of retinal substructures from D-OCT images, IEE Transactions on Biomedical Engineering, Nov. 2019, pp. 3105-3118, vol. 66, No. 11, EMB.

Seon Young Ryu, et al., Combined system of optical coherence tomography and fluorescence spectroscopy based on double-cladding fiber, Optics Letters, pp. 2347-2349, Oct. 15, 2008, vol. 33, No. 20.

Juan Sancho-Dura, et al., Handheld multi-modal imaging for point-of-care skin diagnosis based on akinetic Integrated optics optical coherence tomography, Biophotonics Journal, 2018, pp. 1-6, 2018, Wiley-VCH Verlag, GmbH & Co. KGaA Weinheim.

Tuqiang Xie, et al., Fiber-optic-bundle-based optical coherence tomography, Optics Letters, Jul. 15, 2005, pp. 1803-1805, vol. 30, No. 14.

Gunay Yurtsever, et al., Photonic integrated Mach-Zehnder interferometer with an on-chip reference arm for optical coherence tomography, Biomedical Optics Express, Apr. 1, 2014, pp. 1050-1060, vol. 5, No. 4, OSA.

Chao Zhou, et al., Space-division multiplexing optical coherence tomography, Optics Express, Aug. 12, 2013, pp. 19219-19227, vol. 21, No. 16, OSA.

\* cited by examiner $\ell = +1, s = +1$ $\ell = -1, s = -1$ $\ell = 0, s = +1$ $\ell = 0, s = -1$

FEW-MODE FIBER ENDOSCOPE

CROSS REFERENCE TO RELATED APPLICATIONS

Technical Field

This disclosure relates generally to endoscopic devices and in particular to an optical fiber endoscope employing few-mode optical fiber.

Background

Medical and non-medical applications of imaging endoscopes are well known and their importance to contemporary cardiology, gastroenterology, pulmonology, laparoscopy as well as nondestructive evaluation/nondestructive testing (NDE/NDT) is widely accepted. Given that importance, improvements to endoscopic devices and systems would represent a welcome addition to the art.

SUMMARY

An advance in the art is made according to an aspect of the present disclosure directed to endoscopic devices employing few mode optical fiber.

In contrast to contemporary, prior-art endoscopic devices and systems, devices and systems constructed according to the present disclosure may employ—in addition to few-mode optical fiber—employ a variety of measurement techniques including swept-source techniques, employ widely tunable source(s), include multiple functions, and—in some embodiments—critical complex optical functions may be performed by one or more photonic integrated circuit(s).

An illustrative endoscopic system and structure according to the present disclosure includes an optical receiver selected from the group consisting of spectral domain optical coherence tomography (OCT) receiver, time domain OCT receiver, confocal receiver, fluorescence receiver, and Raman receiver; an endoscope body including fixed distal optics; and a multicore optical fiber optically coupling the fixed distal optics to the receiver.

Accordingly, and in sharp contrast to prior-art devices, devices and systems constructed according to the present disclosure may include: an optical receiver selected from the group consisting of spectral domain optical coherence tomography (OCT) receiver, time domain OCT receiver, confocal receiver, fluorescence receiver, Raman receiver, and swept-source optical coherent tomography (SS-OCT) receiver; an endoscope body including distal optics; and a few-mode optical fiber optically coupling the distal optics to the receiver; wherein the few-mode fiber optical endoscope is configured to optically illuminate a sample in one or more spatial modes and simultaneously detect multiple backscattered spatial modes from the sample and process them such that information about the sample's longitudinal optical properties is produced.

Operationally, and in further sharp contrast to prior-art devices, a method of operating a few-mode fiber endoscopic system includes directing an optical beam to a sample via an optical fiber; collecting light backscattered from the sample; directing the backscattered light to a detector via the optical fiber; and detecting the backscattered light; wherein the directed optical beam is single mode and the collected light is multiple mode. Of particular advantage, the optical fiber employed may be a few-mode optical fiber or a double-clad optical fiber—among others.

Notably, term endoscope is used throughout the disclosure to describe structures according to the present disclosure. Those skilled in the art will readily appreciate that the disclosure is not specifically limited to endoscopes. More particularly, the disclosure and underlying principles herein are equally applicable to catheters, laparoscopes, imaging guidewires as well as other medical and non-medical devices and structures. Accordingly, when the term endoscope is used, it is intended that it be interchangeable with any instrument or system used to examine the inside of something—oftentimes a body for medical reasons. Such instruments advantageously permit the interior of an organ or other cavity of the body. Of further advantage, endoscopes are capable of being inserted directly into an organ for subsequent examination.

BRIEF DESCRIPTION OF THE DRAWING

A more complete understanding of the present disclosure may be realized by reference to the accompanying drawings in which.

DETAILED DESCRIPTION

The following merely illustrates the principles of the disclosure. It will thus be appreciated that those skilled in the art will be able to devise various arrangements which, although not explicitly described or shown herein, embody the principles of the disclosure and are included within its spirit and scope. More particularly, while numerous specific details are set forth, it is understood that embodiments of the disclosure may be practiced without these specific details and in other instances, well-known circuits, structures and techniques have not been shown in order not to obscure the understanding of this disclosure.

Furthermore, all examples and conditional language recited herein are principally intended expressly to be only for pedagogical purposes to aid the reader in understanding the principles of the disclosure and the concepts contributed by the inventor(s) to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently-known equivalents as well as equivalents developed in the future, i.e., any elements developed that perform the same function, regardless of structure.

Thus, for example, it will be appreciated by those skilled in the art that the diagrams herein represent conceptual views of illustrative structures embodying the principles of the invention.

In the claims hereof any element expressed as a means for performing a specified function is intended to encompass any way of performing that function. The invention as defined by such claims resides in the fact that the functionalities provided by the various recited means are combined and brought together in the manner which the claims call for. Applicant thus regards any means which can provide those functionalities as equivalent as those shown herein. Finally, and unless otherwise explicitly specified herein, the drawings are not drawn to scale.

Thus, for example, it will be appreciated by those skilled in the art that the diagrams herein represent conceptual views of illustrative structures embodying the principles of the disclosure.

By way of some additional background, it is noted that there exist a wide variety of optical sensing technologies used in optical systems that employ single mode optical fiber. Some of these systems are interferometric in nature such as optical coherence tomography systems.

Figure 1:
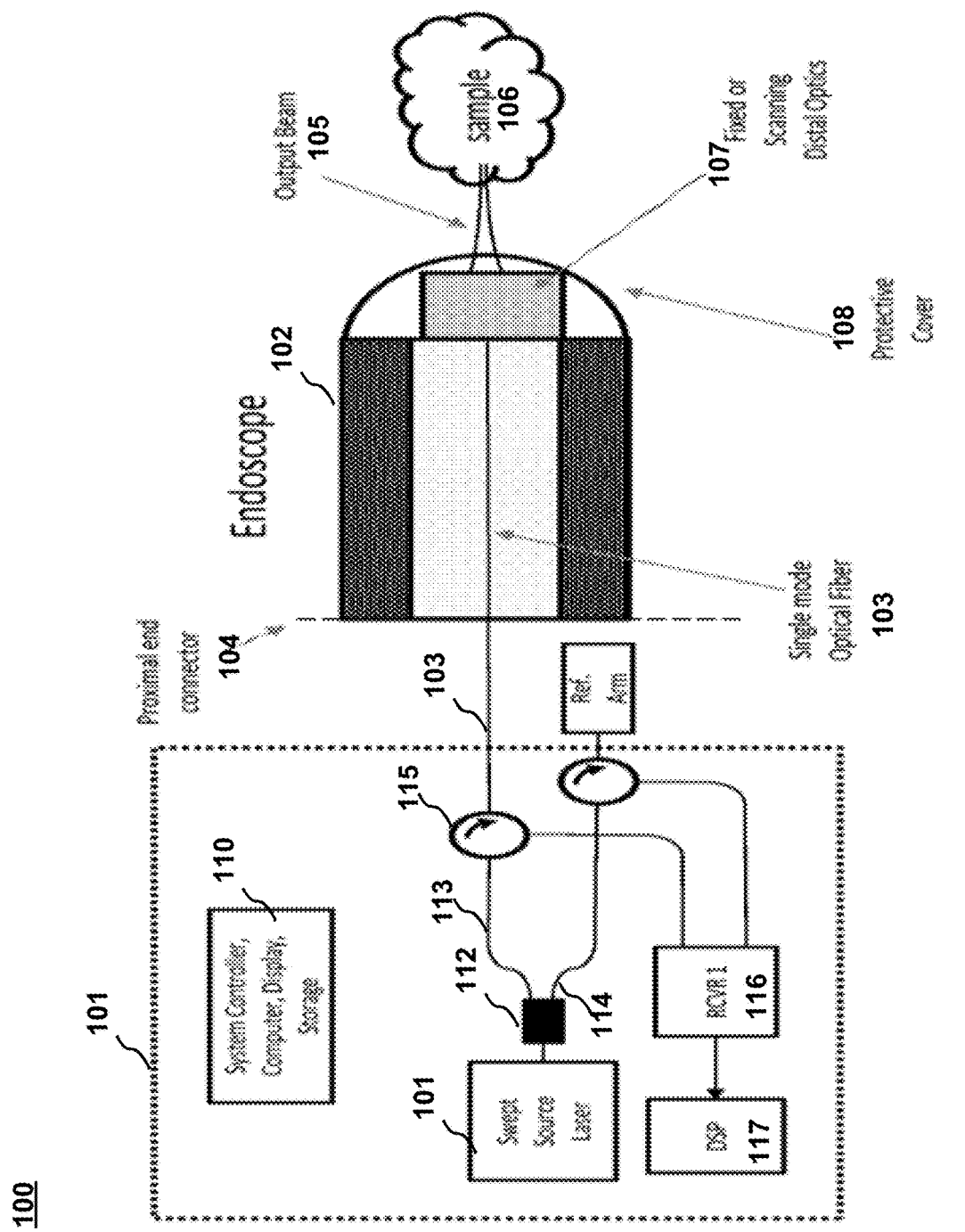
FIG. 1 shows an exemplary swept-source optical coherence tomography (SS-OCT) Prior Art endoscopic system.

Turning now to FIG. 1 there is shown a schematic of an illustrative swept source optical coherence tomography system (SS-OCT) configured as an optical endoscope such as those known in the art. As may be observed from that Figure, such an SS-OCT endoscopic system generally includes source/controller/detector sub-system 101 and an endoscope sub-systems 102 coupled together via a single mode optical fiber 103. While not specifically identified in that Figure, such endoscopes and systems may include an eyepiece, a light post, and an objective assembly. Alternative configurations may include—among other things—an access port for instrument(s) and an "umbilical" connection.

As may be readily understood by those skilled in the art, SS-OCT systems such as that shown schematically in the Figure generally include a system controller 110, a swept source laser 111, a receiver 112 and digital signal processor 113.

In the generalized illustrative schematic depicted, the controller sub system 101 is configured to operate with endoscopic sub system 102 wherein the two sub systems are coupled via single mode optical fiber 103 and proximal end connector 104.

As should be readily apparent the endoscope sub system is designed/configured such that it is readily insertable into a body cavity such that an output beam 105 may be suitably directed to sample 106. Shown further in that Figure with respect to the endoscope subsystem 102 are fixed or scanning distal optics 107 which desirably directs output beam 105 and protective cover 108 which—as its name implies—provides mechanical and other protection to the optics 107 while providing a desirable shape to the distal end of the endoscope. As should be readily understood and appreciated, a number of variations of shape, size, material and configuration are known in the art and advantageously operable in the context of systems constructed according to the present disclosure.

Operationally, the SS-OCT sub system 101 generates source light through the effect of swept source laser 101 which is split by splitter 112 and subsequently directed to sample path 113 or reference path 114. As appreciated, light directed to sample path 113 is conveyed to sample 106 by single mode optical fiber 103 and further by distal optics 107. Light back-scattered/reflected/received from sample is conveyed back to SS-OCT sub-system 101 via single mode optical fiber 103 and directed to receiver 116 and digital signal processor 117 by circulator 115 or other suitable re-directing structure(s).

At this point it is noted and should be readily appreciated that the SS-OCT system illustrated in FIG. 1 is merely illustrative of general principles of such devices. Alternative embodiments, including time domain OCT (TD-OCT), spectral domain OCT (SD-OCT) and other non-OCT modalities including both interferometric and non-interferometric are also known in the art and may be employed as application needs dictate. More particularly, fluorescence, Raman spectroscopy, near infrared spectroscopy and confocal microscopy sensing and imaging are known and understood technologies and may be employed by those skilled in the art constructing/configuring such structures/devices/systems. In addition, while FIG. 1 shows an illustrative endoscopic embodiment, alternative embodiments such as catheters, guidewires, laparoscopes, microscopes, and other embodiments/configurations are understood.

Worth noting at this point is the fact that in the prior art embodiment shown, not all the light altered and backscattered/reflected from the sample is collected from the illuminating single mode fiber. After the scattering of the source light from within the sample only that light that arrives back at the single-mode fiber which is in the fundamental mode of the single mode fiber is coupled and transmitted back to the OCT receiver. If additional modes of light could be collected and coupled to an electro-optical receiver, then additional information about the sample's optical properties could be extracted.

Figure 2:
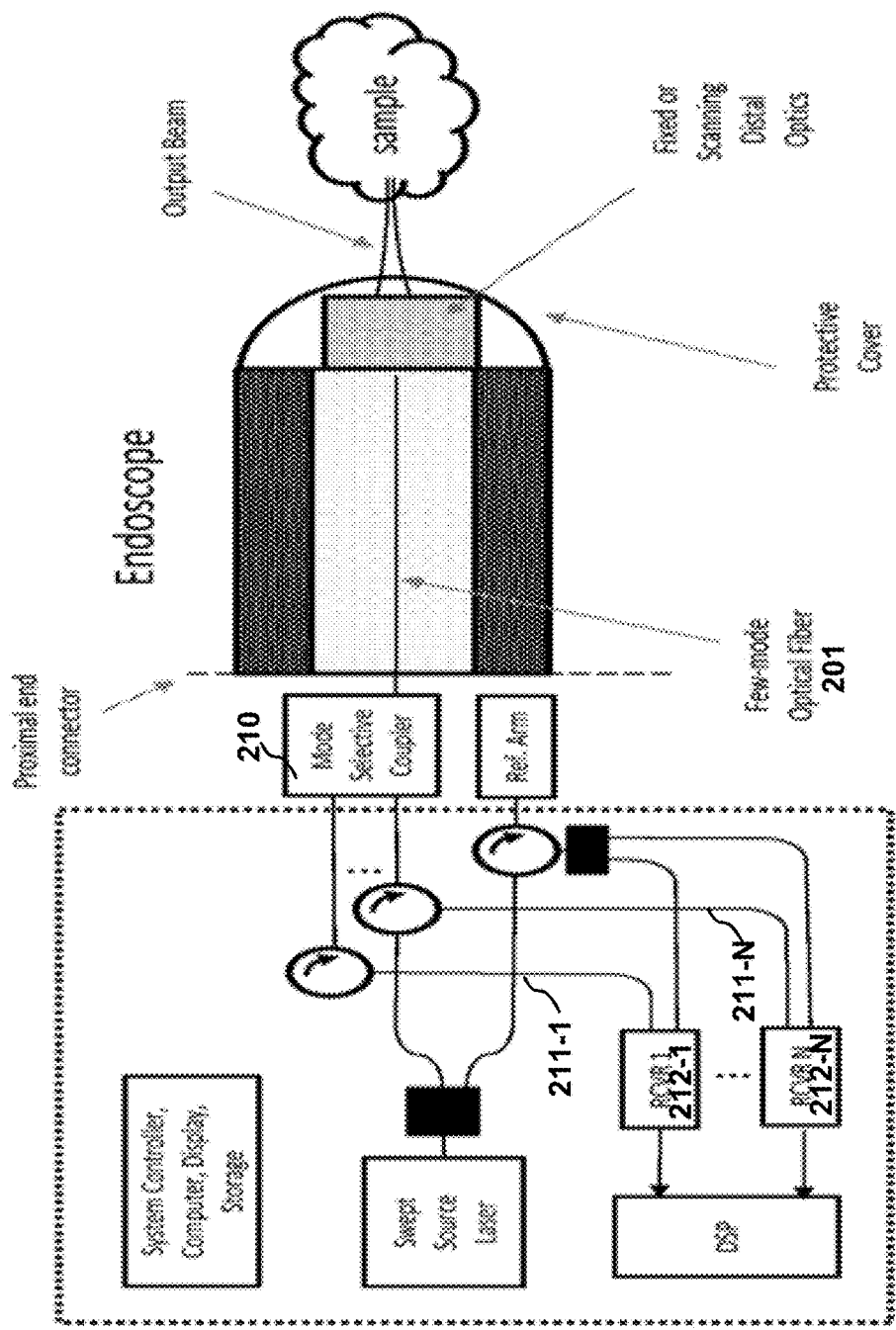
FIG. 2 shows an illustrative SS-OCT endoscopic system employing few-mode optical fiber according to an aspect of the present disclosure.

FIG. 2 illustratively shows one embodiment of an SS-OCT endoscopic system 200 according to the present disclosure that achieves multi-modal spatial detection. Notably, a few-mode optical fiber is used. Note further that while the word "few-mode" is used herein—there is no upper limit on the number of modes that are applicable to the concepts disclosed herein.

With continued reference to FIG. 2, light from swept source laser is coupled into a mode selective coupler 210 (sometimes called a mode selective photonic lantern). As will be readily understood by those skilled in the art, there exist a number and variety of types of photonic lanterns or mode selective couplers including fiber devices, free space optical devices, and fiber gratings—among others—that may be employed with structures according to the present disclosure.

Operationally—and in one particular, illustrative embodiment, the laser source light is only coupled into the fundamental circularly symmetric mode LPO 1 of the few-mode fiber. As will be appreciated, other approaches are possible and contemplated according to the present disclosure including using other modes for illumination or illuminating more than one mode simultaneously.

In the illustrative example shown, the fundamental mode of light is directed onto the sample. Back scattered light is coupled into one or more of the modes of the few-mode fiber 201, and each of those modes is separately detected by spatially extracting the modes from the few-mode fiber 201 to individual single-mode fibers 211-1 . . . 211-N through the effect of mode selective coupler 210. The individual modes are then conveyed to a number of receivers 212-1 . . . 212-N where they are detected such that information may be extracted by digital signal processor.

As will be appreciated, there exist a number of possible approaches to construct a mode selective coupler—as is known in the art—including all fiber approaches, free-space optical approaches, fiber bragg gratings, long period fiber gratings and integrated optical approaches. In the illustrative example shown in FIG. 2, the SS-OCT system employs a receiver 212-1 . . . 212-N for each mode of the few-mode fiber. Notably, one particularly attractive approach to construct a compact and low cost multiple receiver is to employ integrated optics as well as other approaches. Finally, and as noted above, there are other types of interferometric and non-interferometric optical receivers that may be employed instead of the SS-OCT embodiment shown in the Figure. Such alternatives include Raman, near-infrared spectroscopy, and fluorescence—as well as other optical modalities.

Figure 3A:
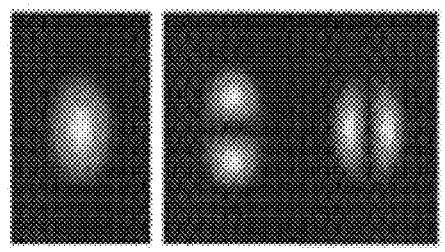
FIG. 3(A) shows several illustrative examples of near-field mode profiles of few-mode optical fiber(s)
Figure 3A:
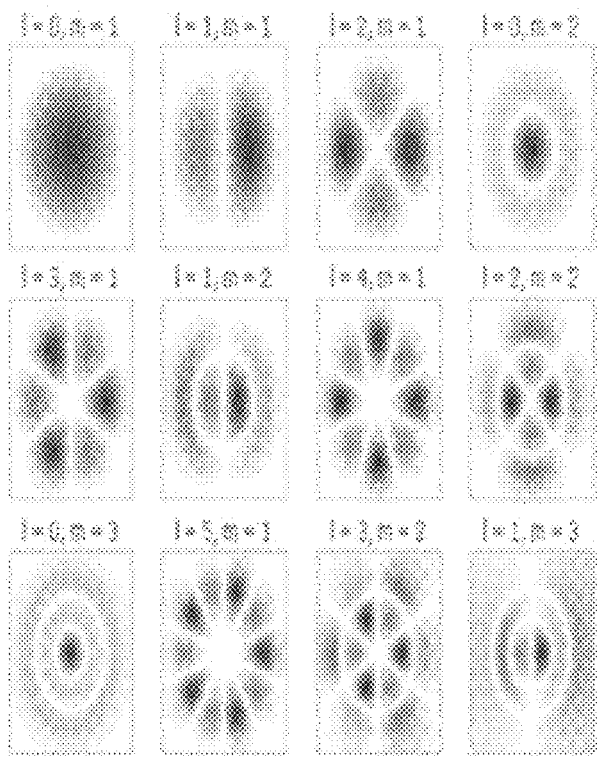

FIG. 3(A) shows some illustrative examples of near field profiles of some typical lower order modes in a few-mode optical fiber as is well known in the art. With reference to that Figure, it may be observed at the top portion shows the LPO 1 mode, the LPlla mode, and the LPllb mode. The bottom portion of the Figure shows additional modes that are possible according to further aspects of the present disclosure.

Figure 3B:
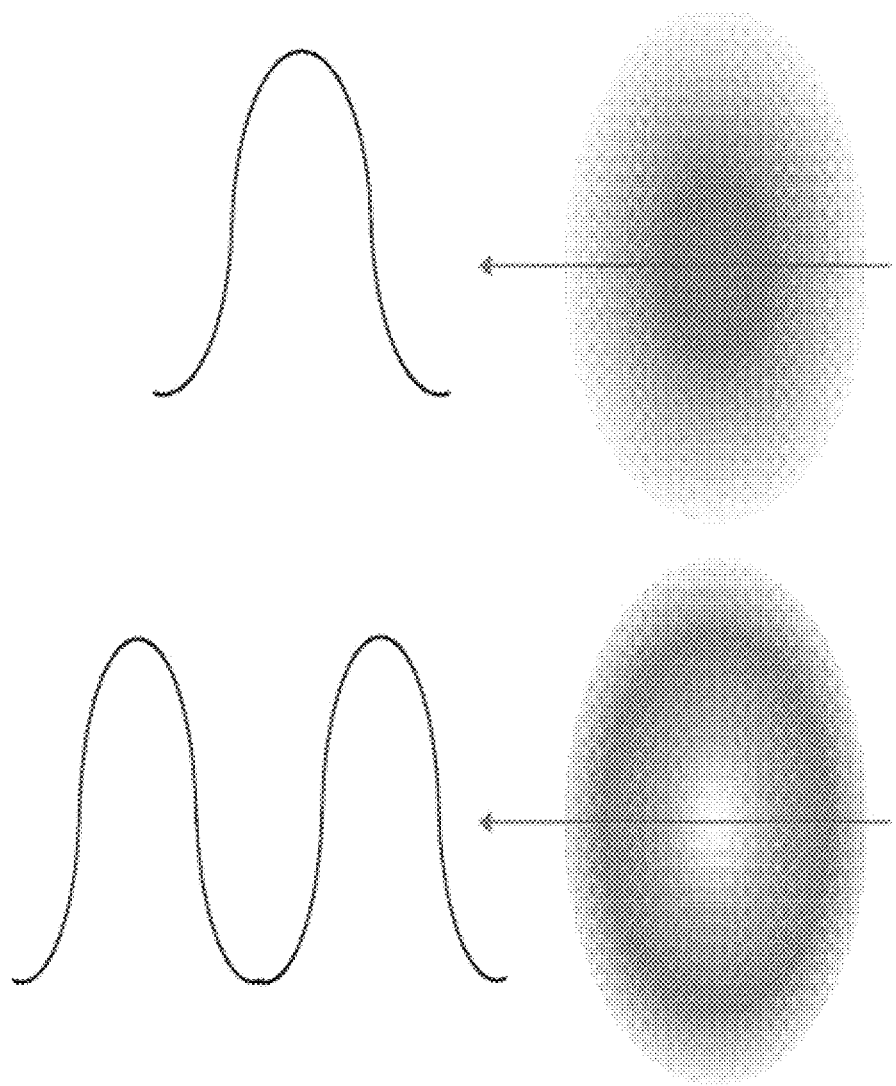
FIG. 3(B) shows an illustrative example of a circularly symmetric low-order mode and a circularly symmetric high-order mode.

In one illustrative embodiment, only two modes are utilized namely, a low-order circularly symmetric mode with a peak intensity on-axis at the beam waist and a higher-order mode that is also circularly symmetric with a null intensity on-axis at the beam waist within the sample. This is conceptually illustrated in FIG. 3(B) where the top portion of the Figure depicts the 2D peak intensity on-axis and the bottom portion of the Figure depicts the 2D null intensity on-axis. Shown further in that Figure to the left of each of the 2D intensity plots are 1D cross sections of intensity vs x-axis cuts the center. Note that one concept this Figure is intended to illustrate is that, for example a normal SS-OCT system illuminates in the LPO 1 mode in an approximate Gaussian beam profile at the beam waist within the sample. Back scattered light is coupled back into the SS-OCT receiver and axial optical profile information can be obtained about the samples optical characteristics. By also collecting a high-order mode such as shown in the bottom portion of FIG. 3(B), additional information on the samples optical properties including increased contrast imaging and obtaining additional information about the sample is possible. Such approaches are known to be beneficial in microscopy and are applied here through a few-mode fiber.

As may be appreciated, in alternative, illustrative embodiments of systems according to the present disclosure, a dual polarization OCT receiver is used for each of the detected modes since there are often two distinct polarization modes and a dual polarization receiver can implement either polarization diversity or polarization sensitive imaging as is known in the art.

Figure 3C:
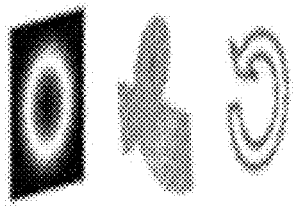
FIG. 3(C) shows illustratively four modes having distinct values of orbital angular momentum (OAM) (1) and spin (s)
Figure 3C:
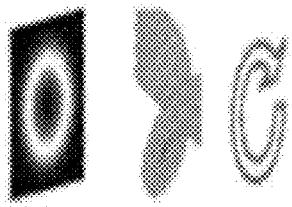
Figure 3C:
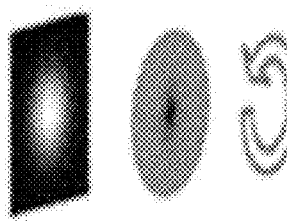
Figure 3C:
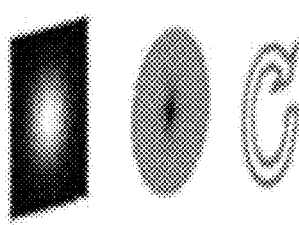

Additionally, in one illustrative embodiment of systems according to the present disclosure, orbital angular momentum (OAM) transmission and detection is utilized for obtaining additional information about the samples optical properties compared to conventional single-mode SS-OCT systems. Using OAM properties of light propagation one can create substantially orthogonal and spatially distinct patterns of light, and multiplex and demultiplex them using a mode-selective coupler-like device into separate SS-OCT receivers or other types of optical receivers. One particularly attractive property of angular momentum transmission in fiber is that some low order modes look very similar to that shown in FIG. 3B and are shown in FIG. 3C for the lower order topological charge (1) and spin (s).

As will be appreciated, there exist various approaches to multiplexing and demultiplexing OAM modes including spatial light modulators, conventional free-space optics (lenses, waveplates, polarizers, masks, etc), and fiber couplers. Additionally, there exist a variety of types of transmission fiber(s) that are suitable for propagation of OAM modes including vortex fiber, and ring fibers—among other types of multimode fibers. Advantageously, OAM beams are characterized by minimal crosstalk and orthogonality. Consequently, they are well suited for OCT and other optical sensor and imaging modalities using transmitter and receiver structures according to the present disclosure.

Figure 4:
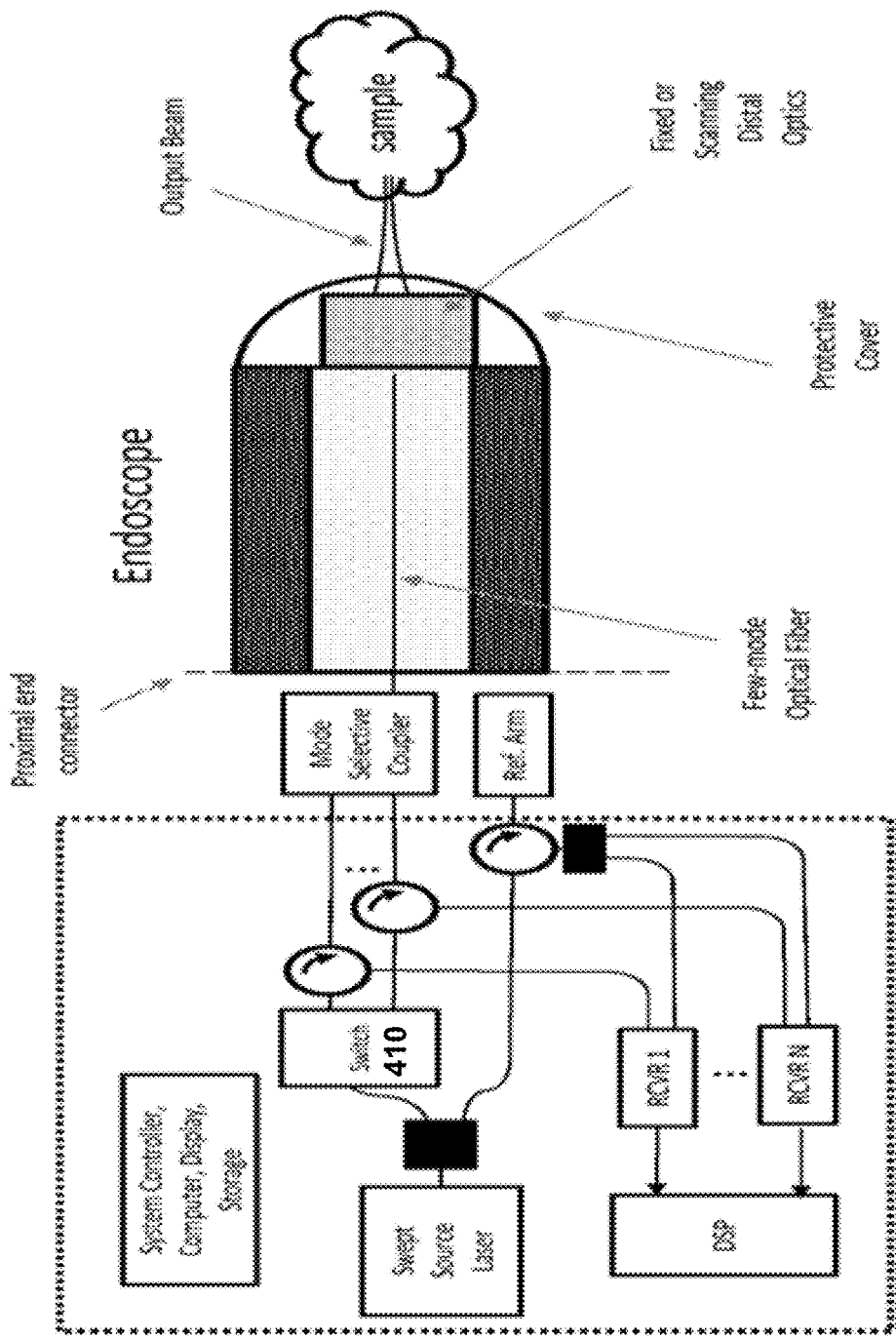
FIG. 4 shows an illustrative SS-OCT endoscopic system employing a few-mode optical fiber and a spatial switch according to an aspect of the present disclosure.

Turning now to FIG. 4, there is shown an alternative illustrative example of an SS-OCT endoscopic system 400 according to the present disclosure employing a few-mode optical fiber and a 1:N spatial switch 410 interposed between a laser source and a mode selective coupler. Advantageously, by employing such a switch, the system illustrated is capable of selecting which mode is excited on the transmitting side. Of further advantage, it also enables one to make multiple measurements of a sample's optical properties by sequentially illuminating a single transmit spatial mode and detecting multiple backscattered modes.

Figure 5:
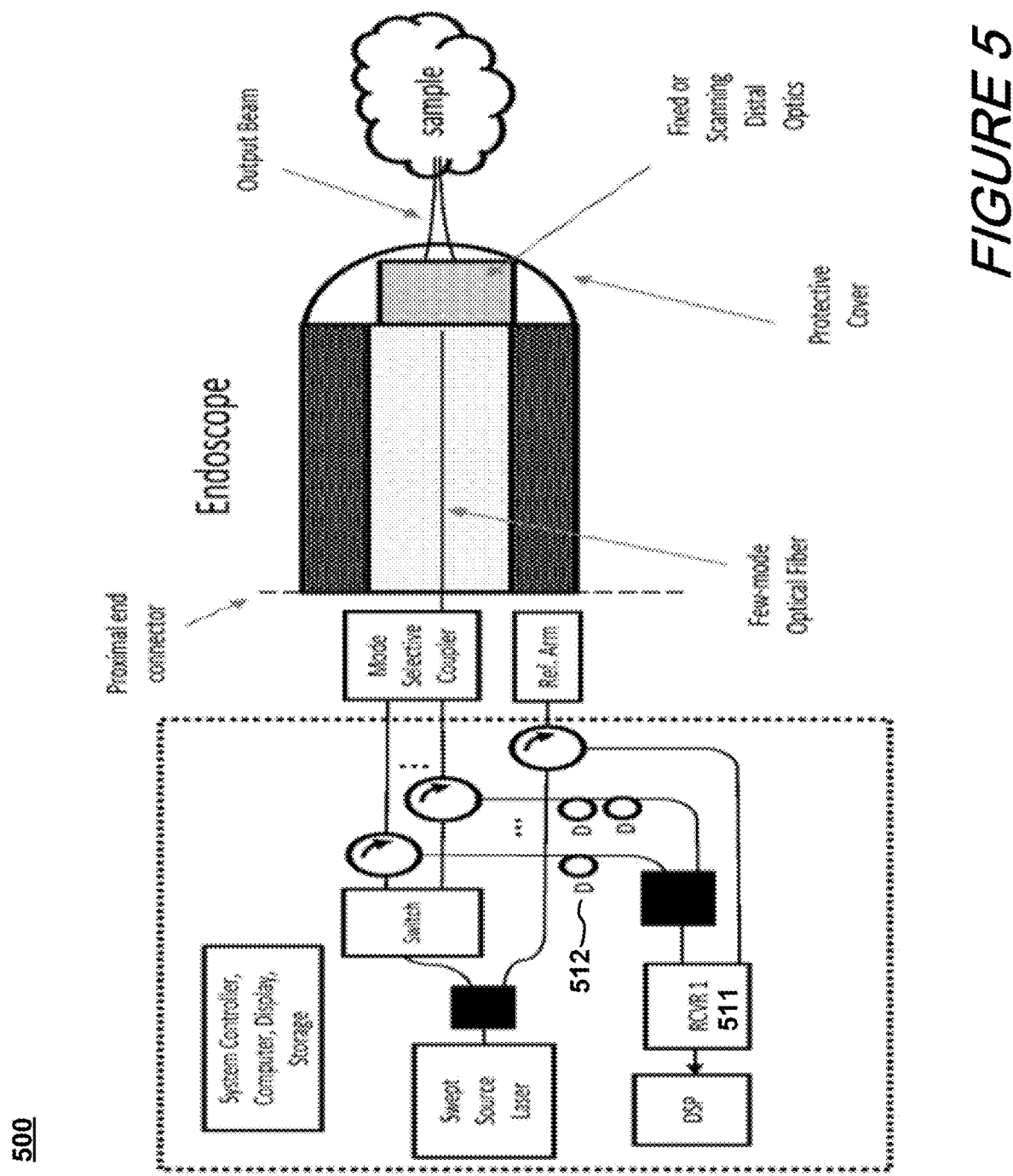
FIG. 5 shows an illustrative SS-OCT endoscopic system employing a few-mode optical fiber and a single receiver according to an aspect of the present disclosure.

FIG. 5, shows yet another illustrative embodiment of an SS-OCT system 500—similar to that depicted in FIG. 4—but only one receiver 511 is used and the information from the individual received fiber modes is uniquely delayed in time—through the effect of delay elements 512—and combined. By delaying each of the received modes "D" the information from each mode is electro-optically detected at separate and distinct if. frequencies. Advantageously—for the configuration depicted in FIG. 5—only one, single receiver 511 is required.

Figure 6:
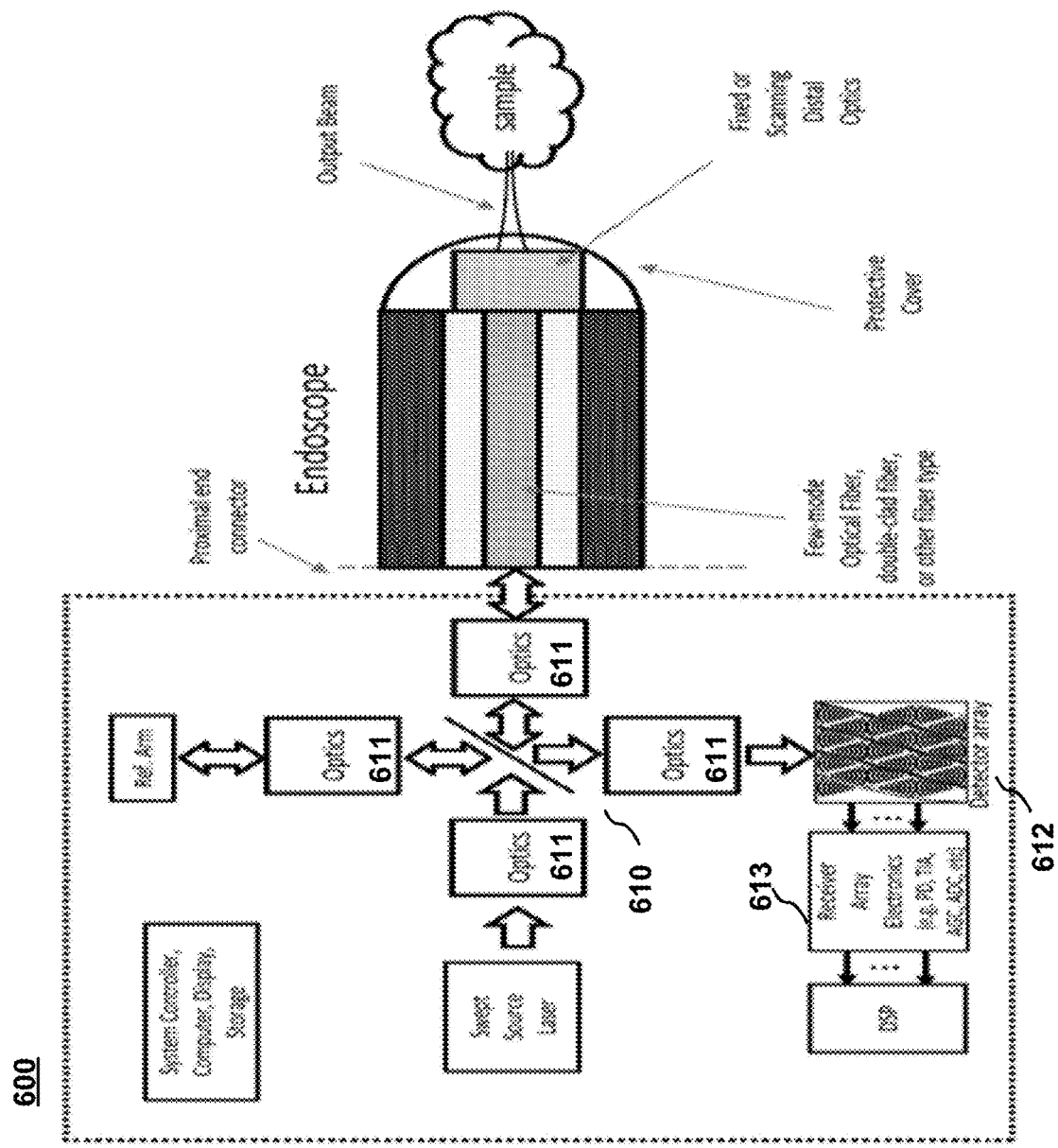
FIG. 6 shows an illustrative SS-OCT endoscopic system employing a few-mode optical fiber and a detector array according to an aspect of the present disclosure.

FIG. 6, shows another illustrative embodiment of an SS-OCT endoscopic system 600 wherein a photonic array 610 is used to implement the photonic lantern or mode selective coupler function electronically. In the illustrative example shown, the laser source is coupled into a few-mode fiber optical endoscope using bulk optical devices 611 and also light is coupled from the laser source to a reference arm. Light backscattered by the sample and reference arm are combined in a beam splitter and sent onto a detector array 612. Advantageously, there exist a variety of types/configurations of detector arrays that may be employed including a photonic integrated circuits having array(s) of surface grating couplers. The detector array 612 is in optical communication with a receiver array 613 that may include photo detectors (PDP, transimpedance amplifiers (TIAs), automatic gain control (AGC), and analog to digital converters (ADCs). The output of the receiver array is directed to a DSP unit that electronically processes the functions in a way that can mimic a mode selective coupler or many other types of functions.

Figure 7:
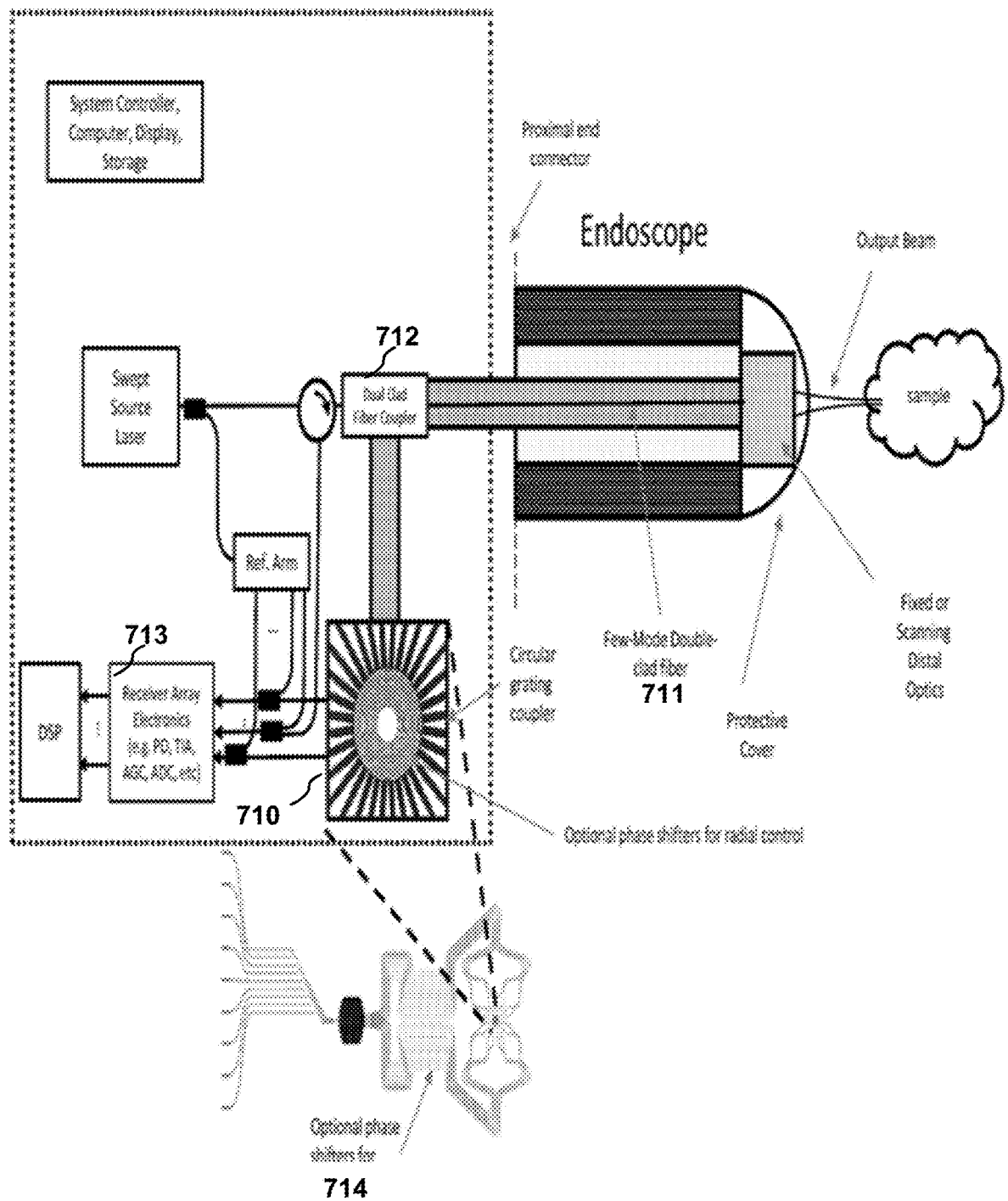
FIG. 7 shows an illustrative SS-OCT endoscopic system employing a few-mode, double-clad optical fiber and a circular grating coupler according to an aspect of the present disclosure.

Finally, FIG. 7, shows another illustrative embodiment of an SS-OCT endoscopic system 700 wherein a circularly symmetric grating coupler 710 is used along with a double clad fiber 711. As may be observed in that Figure, light from a swept laser source is coupled via single mode fiber to a dual clad fiber coupler 712. One port of the coupler contains a single mode fiber and another port contains a few-mode multimode fiber. The single mode light is coupled along the endoscope and within the single mode to the distal end and illuminates the sample. Reflected light in the same fundamental single mode is collected along with light scattered into the outer modes of the double clad fiber 711. The dual clad fiber coupler 712 directs part of this light, the light in the outer clad, to the circularly symmetric grating coupler 710 which then couples to a receiver array 713. Light from the signal mode fiber is directed via a circulator also to the receiver array 713.

As should be appreciated, such a circular grating coupler 710 may be constructed as a photonic integrated circuit using a large grating coupler that has grooves arranged in concentric circles. The grating is "fed" by an array of radially directed waveguides. These waveguides are all connected to a single input/output waveguide by one or more couplers.

Shown further are optional phase shifters 714. By placing controllable phase shifters in the waveguides, one can control the azimuthal phase distribution emanating from the grating coupler. However, one cannot control the radial phase distribution via control of the waveguide phases. If a controllable radial phase distribution is needed, then one can insert short phase shifters inside the grating coupler in a circular pattern. For example, there may be a few grating grooves, a short section of tunable phase shifter, more grating grooves, another short section of tunable phase shifter, etc. This approach extracts orthogonal angular momentum modes and is efficient for reflected light that has substantial circular symmetry. For simplicity, output wave guides shown in the exploded view of the circular grating coupler 710 are not shown coupled into the reference arm light and the receiver array. Advantageously, and as will be readily appreciated, the detector shown in FIG. 7 can also be employed for orbital angular momentum OCT as described previously.

At this point those skilled in the art will readily appreciate that while the methods, techniques and structures according to the present disclosure have been described with respect to particular implementations and/or embodiments, those skilled in the art will recognize that the disclosure is not so limited. In particular—and by way of specific example only—the SS-OCT embodiments shown herein do explicitly show lateral or rotational imaging or pull-back mechanisms as is known in the art. Of course, both proximal and/or distal active and/or passive optics are contemplated as part of this disclosure. Accordingly, the scope of the disclosure should only be limited by the claims appended hereto.

The invention claimed is:

1. A few-mode fiber optical endoscope system comprising:
    an optical source that generates source light;
    an optical redirecting device having an input optically coupled to the optical source and an output optically coupled to a mode selective coupler;
    an endoscope body comprising a few-mode optical fiber that is optically coupled to the optical source, the few-mode optical fiber transmitting the source light to a sample and coupling backscattered light from the sample to the mode selective coupler, the mode selective coupler extracting light from the coupled backscattered light into one or more spatially separated modes to produce at least two individual light modes comprising a low-order mode and a higher-order mode; and
    an optical receiver comprising a first optical receiver optically coupled to the mode selective coupler and configured to detect the low-order mode and a second optical receiver optically coupled to the mode selective coupler and configured to detect the higher-order, the optical receiver further configured to process the detected low-order mode and the higher-order mode thereby achieving multi-modal spatial detection such that information about the sample's optical properties is produced.

2. The few-mode fiber optical endoscope system of claim 1 wherein the mode selective coupler is configured to spatially extract N modes from the few-mode fiber; and wherein the optical receiver comprises a number (N) of individual, respective receivers, one for each of the modes, each receiver being optically connected to the mode selective coupler by an optical fiber.

3. The few-mode fiber optical endoscope system of claim 2 wherein the optical fiber(s) connecting the mode selective coupler to the individual receivers is a single mode optical fiber.

4. The few-mode fiber optical endoscope system of claim 2 further comprising:
    a 1:N spatial switch interposed between the optical source and the mode selective coupler, said switch configured such that the system is configurable to select which mode is excited on a transmitting side of the mode selective coupler.

5. The few-mode fiber optical endoscope system of claim 1 wherein the mode selective coupler comprises an electronically configurable photonic array.

6. The few-mode fiber optical endoscope system of claim 1 wherein the few-mode fiber is few-mode, double-clad optical fiber and wherein the mode selective coupler comprises a circular grating coupler and a dual clad fiber coupler.

7. The few-mode fiber optical endoscope system of claim 6 further comprising:
    a number of phase shifters positioned within the circular grating coupler and configured such that angular momentum modes of light are extracted.

8. The few-mode optical endoscope system of claim 1 further comprising a photonic integrated circuit (PIC) onto which is fabricated the optical receiver.

9. The few-mode optical endoscope system of claim 8 further comprising a vertical cavity surface emitting laser (VCSEL) fabricated onto the PIC with the optical receiver.

10. A few-mode fiber optical endoscope system comprising:
    an optical source that generates source light;
    an optical redirecting device having an input optically coupled to the optical source and an output optically coupled to a mode selective coupler;
    an endoscope body comprising a few-mode optical fiber that is optically coupled to the optical source, the few-mode optical fiber transmitting the source light to a sample and coupling backscattered light from the sample into the few-mode fiber and conveying the coupled backscattered light to the mode selective coupler, the mode selective coupler extracting light from the coupled backscattered light into one or more spatially separated modes to produce at least two individual light modes;
    an optical receiver optically coupled to the mode selective coupler; and
    a delay element positioned between the mode selective coupler and the optical receiver and configured such that each of the at least two individual light modes is uniquely delayed in time such that information about the sample's optical properties from each of the at least two individual light modes is electro-optically detected by the optical receiver at distinct intermediate frequencies.

11. The few-mode fiber optical endoscope system of claim 1 wherein the information about the sample's optical properties comprises axial profile information about the sample.

12. The few-mode fiber optical endoscope system of claim 1 wherein the information about the sample's optical properties comprises increased contrast imaging information about the sample.

13. The few-mode fiber optical endoscope system of claim 1 wherein the one or more spatially separated modes comprises three or more spatially separated modes.

* * * * *